United States Patent
Strul et al.

(10) Patent No.: US 6,358,273 B1
(45) Date of Patent: Mar. 19, 2002

(54) SOFT TISSUE HEATING APPARATUS WITH INDEPENDENT, COOPERATIVE HEATING SOURCES

(75) Inventors: Bruno Strul, Portola Valley; Hugh R. Sharkey, Woodside; Daren L. Stewart, Belmont, all of CA (US)

(73) Assignee: Oratec Inventions, Inc., Menlo Park, CA (US)

( * ) Notice: Subject to any disclaimer, the term of this patent is extended or adjusted under 35 U.S.C. 154(b) by 0 days.

(21) Appl. No.: 09/289,459

(22) Filed: Apr. 9, 1999

(51) Int. Cl.[7] ............................. A61F 7/00; A61F 2/00
(52) U.S. Cl. ...................... 607/96; 607/98; 607/101; 607/105
(58) Field of Search .................. 607/96, 101, 102, 607/103, 104, 105, 116, 115; 606/41–42, 45, 49, 27–29, 31

(56) References Cited

U.S. PATENT DOCUMENTS

| | | |
|---|---|---|
| 164,184 A | 8/1875 | Kidder |
| 300,155 A | 6/1884 | Starr |
| 371,664 A | 10/1887 | Brannan et al. |
| 452,220 A | 5/1891 | Gunning |
| 1,314,855 A | 9/1919 | Carpenter |
| 1,366,756 A | 1/1921 | Wappler |
| 1,731,627 A | 10/1929 | Johnson et al. |
| 1,735,271 A | 12/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 11/1934 | Kimble |
| 2,002,594 A | 5/1935 | Wappler et al. |
| 2,004,559 A | 6/1935 | Wappler et al. |
| 2,050,904 A | 8/1936 | Trice |
| 2,056,377 A | 10/1936 | Wappler |
| 2,224,464 A | 12/1940 | Wolf |
| 2,275,167 A | 3/1942 | Bierman |

(List continued on next page.)

FOREIGN PATENT DOCUMENTS

| | | |
|---|---|---|
| GB | 2160102 A | 12/1985 |
| WO | WO 94/26228 | 11/1994 |

OTHER PUBLICATIONS

Product Sheet—The ArthroWand CoVac; ArthroCare Corporation, 1998.
Product Sheet—CAPS and CAPS X ArthroWands For Capsular Shrinkage; ArthroCare Corporation, 1998.
Lee Beadling, *Bi–Polar electrosurgical devices: Sculpting the future of arthroscopy*, Orthopedics Today, Jan. 1997, vol. 17, No. 1, Slack, Inc., Medical Publisher.

*Primary Examiner*—Roy Gibson
(74) *Attorney, Agent, or Firm*—Flehr Hohbach Test Albritton & Herbert LLP

(57) ABSTRACT

A medical probe for the heating of soft tissue, such as collagen tissue, wherein the medical probe has an elongated body with a proximal and distal end, a heating source, an RF electrode. Optional components include a thermocouple, and an insulative sleeve. The probe's elongated body is preferably hollow and flexible. The RF electrode and the heating source are powered by independently controlled power sources and cooperate to maintain a constant and smooth temperature to the distal end of the RF electrode. The heating source may be a contained liquid, such as saline, or an electrothermal mass, such as a ferrite, a toroid, a resistive element, or the like. Current induced from the conductor to the heating source creates heat in the heating source. The thermocouple measures the temperature of the heating source and adjusts the power to the conductor to maintain the heating source's temperature.

18 Claims, 3 Drawing Sheets

U.S. PATENT DOCUMENTS

| | | |
|---|---|---|
| 2,888,928 A | 6/1959 | Seiger |
| 3,152,590 A | 10/1964 | Zurdo et al. |
| 3,163,165 A | 12/1964 | Isakawa |
| 3,460,539 A | 8/1969 | Anhalt, Sr. |
| 3,595,239 A | 7/1971 | Petersen |
| 3,768,482 A | 10/1973 | Shaw |
| 3,828,780 A | 8/1974 | Morrison, Jr. |
| 3,870,047 A | 3/1975 | Gonser |
| 3,901,242 A | 8/1975 | Storz |
| 3,902,494 A | 9/1975 | Haberlen et al. |
| 3,920,021 A | 11/1975 | Hiltebrandt |
| 3,920,022 A | 11/1975 | Pastor |
| 3,938,527 A | 2/1976 | Rioux et al. |
| 3,987,795 A | 10/1976 | Morrison |
| 3,993,048 A | 11/1976 | Francis |
| 4,033,351 A | 7/1977 | Hetzel |
| 4,171,700 A | 10/1979 | Farin |
| 4,202,337 A | 5/1980 | Hren et al. |
| 4,228,800 A | 10/1980 | Degler, Jr. et al. |
| 4,244,371 A | 1/1981 | Farin |
| 4,326,529 A | 4/1982 | Doss et al. |
| 4,483,338 A | 11/1984 | Bloom et al. |
| 4,532,924 A | 8/1985 | Auth et al. |
| 4,567,890 A | 2/1986 | Ohta et al. |
| 4,674,499 A | 6/1987 | Pao |
| 4,686,980 A | 8/1987 | Williams et al. |
| 4,805,616 A | 2/1989 | Pao |
| 4,832,048 A | 5/1989 | Cohen |
| 4,927,420 A | 5/1990 | Newkirk et al. |
| 4,932,952 A | 6/1990 | Wojciechowicz, Jr. |
| 4,936,301 A | 6/1990 | Rexroth et al. |
| 4,976,711 A | 12/1990 | Parins et al. |
| 4,998,933 A | 3/1991 | Eggers et al. |
| 5,007,908 A | 4/1991 | Rydell |
| 5,009,656 A | 4/1991 | Reimels |
| 5,013,312 A | 5/1991 | Parins et al. |
| 5,025,811 A | 6/1991 | Dobrogowski et al. |
| 5,057,107 A | 10/1991 | Parins et al. |
| 5,071,419 A | 12/1991 | Rydell et al. |
| 5,078,717 A | 1/1992 | Parins et al. |
| 5,098,431 A | 3/1992 | Rydell |
| RE33,925 E | 5/1992 | Bales et al. |
| 5,122,137 A | 6/1992 | Lennox |
| 5,125,928 A | 6/1992 | Parins et al. |
| 5,171,311 A | 12/1992 | Rydell et al. |
| 5,178,620 A | 1/1993 | Eggers et al. |
| 5,192,280 A | 3/1993 | Parins |
| 5,197,964 A | 3/1993 | Parins |
| 5,201,900 A | 4/1993 | Nardella |
| 5,221,281 A | 6/1993 | Klicek |
| 5,241,224 A | 8/1993 | Pedersen et al. |
| 5,269,780 A | 12/1993 | Roos |
| 5,277,696 A | 1/1994 | Hagen |
| 5,281,216 A | 1/1994 | Klicek |
| 5,281,218 A | 1/1994 | Imran |
| 5,282,799 A | 2/1994 | Rydell |
| 5,300,069 A | 4/1994 | Hunsberger et al. |
| 5,306,274 A * | 4/1994 | Long .......................... 606/28 |
| 5,308,311 A | 5/1994 | Eggers et al. |
| 5,356,408 A | 10/1994 | Rydell |
| 5,366,443 A | 11/1994 | Eggers et al. |
| 5,382,247 A | 1/1995 | Cimino et al. |
| 5,395,363 A | 3/1995 | Billings et al. |
| 5,395,369 A | 3/1995 | McBrayer et al. |
| 5,396,900 A | 3/1995 | Slater et al. |
| 5,403,311 A | 4/1995 | Abele et al. |
| 5,409,008 A | 4/1995 | Svenson et al. |
| 5,419,767 A | 5/1995 | Eggers et al. |
| 5,441,499 A | 8/1995 | Fritzsch |
| 5,451,224 A | 9/1995 | Goble et al. |
| 5,458,596 A | 10/1995 | Lax et al. |
| 5,458,597 A | 10/1995 | Edwards et al. |
| 5,472,441 A | 12/1995 | Edwards et al. |
| 5,484,435 A | 1/1996 | Fleenor et al. |
| 5,505,730 A | 4/1996 | Edwards |
| 5,507,743 A * | 4/1996 | Edwards et al. ............... 606/41 |
| 5,514,130 A | 5/1996 | Baker |
| 5,520,685 A | 5/1996 | Wojciechowicz |
| 5,531,744 A | 7/1996 | Nardella et al. |
| 5,549,606 A | 8/1996 | McBrayer et al. |
| 5,556,397 A | 9/1996 | Long et al. |
| 5,558,672 A | 9/1996 | Edwards et al. |
| 5,562,659 A | 10/1996 | Morris |
| 5,562,720 A | 10/1996 | Stern et al. |
| 5,569,242 A | 10/1996 | Lax et al. |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,575,788 A | 11/1996 | Baker et al. |
| 5,599,346 A | 2/1997 | Edwards et al. |
| 5,599,350 A | 2/1997 | Schulze et al. |
| 5,637,090 A | 6/1997 | McGee et al. |
| 5,643,197 A | 7/1997 | Brucker et al. |
| 5,643,255 A | 7/1997 | Organ |
| 5,647,869 A | 7/1997 | Goble et al. |
| 5,658,278 A | 8/1997 | Imran et al. |
| 5,662,680 A | 9/1997 | Desai |
| 5,673,695 A | 10/1997 | McGee et al. |
| 5,676,662 A | 10/1997 | Fleischhacker et al. |
| 5,676,693 A | 10/1997 | LaFontaine |
| 5,680,860 A | 10/1997 | Imran |
| 5,681,282 A | 10/1997 | Eggers et al. |
| 5,681,308 A | 10/1997 | Edwards et al. |
| 5,683,366 A | 11/1997 | Eggers et al. |
| 5,683,384 A | 11/1997 | Gough et al. |
| 5,683,385 A | 11/1997 | Kortenbach et al. |
| 5,687,723 A | 11/1997 | Avitall |
| 5,688,267 A | 11/1997 | Panescu et al. |
| 5,688,270 A | 11/1997 | Yates et al. |
| 5,693,052 A | 12/1997 | Weaver |
| 5,693,078 A | 12/1997 | Desai et al. |
| 5,694,945 A | 12/1997 | Ben-Haim |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,925 A | 12/1997 | Taylor |
| 5,697,927 A | 12/1997 | Imran et al. |
| 5,697,949 A | 12/1997 | Giurtino et al. |
| 5,700,262 A | 12/1997 | Acosta et al. |
| 5,702,390 A | 12/1997 | Austin et al. |
| 5,730,742 A | 3/1998 | Wojciechowicz |
| 5,743,903 A | 4/1998 | Stern et al. |
| 5,755,664 A | 5/1998 | Rubenstein |
| 5,766,153 A | 6/1998 | Eggers et al. |
| 5,779,701 A | 7/1998 | McBrayer et al. |
| 5,785,705 A * | 7/1998 | Baker .......................... 606/32 |
| H1745 H | 8/1998 | Paraschac |
| 5,797,903 A | 8/1998 | Swanson et al. |
| 5,800,482 A | 9/1998 | Pomeranz et al. |
| 5,807,395 A | 9/1998 | Mulier et al. |
| 5,810,764 A | 9/1998 | Eggers et al. |
| 5,810,805 A | 9/1998 | Sutcu et al. |
| 5,810,809 A | 9/1998 | Rydell |
| 5,814,043 A | 9/1998 | Shapeton |
| 5,827,275 A | 10/1998 | Morris |
| 5,843,075 A | 12/1998 | Taylor |
| 5,843,080 A | 12/1998 | Fleenor et al. |
| 5,846,240 A | 12/1998 | Kortenbach et al. |
| 5,855,061 A | 1/1999 | Malis et al. |
| 5,868,737 A | 2/1999 | Taylor et al. |
| 6,056,747 A * | 5/2000 | Saadat et al. ................. 606/50 |
| 6,135,999 A | 10/2000 | Fanton et al. |

\* cited by examiner

SOFT TISSUE HEATING APPARATUS WITH INDEPENDENT, COOPERATIVE HEATING SOURCES

FIELD OF INVENTION

This invention relates generally to medical probes used for contracting soft tissue, and more particularly, to medical probes for shrinking damaged collagen tissue by applying heat.

BACKGROUND

Medical probes for the rehabilitative heat treatment of damaged soft tissues are known in the art. Examples of these probes include laser probes and RF heated probes. While these tools meet the basic need for rehabilitative heat treatment of soft tissues, such as collagen tissues, many suffer from temperature over-shoot and under-shoot causing unpredictable results in the heating of soft tissue.

Soft tissue is the most abundant tissue in the human body. Most soft tissue is collagen—over 90% of the organic matter in tendon, ligament, and bone is collagen. The connective tissue in joints is soft tissue, generally collagen tissue. When soft tissue in a joint is damaged, the healing process is often long and painful.

Well known treatments for addressing soft tissue damage in joints include strengthening exercises, open surgery, and arthroscopic techniques. Using current treatments, many people with injured joints suffer from prolonged pain, loss of motion, nerve injury, and some develop osteoarthritis. The soft tissue in many injured joints never heals enough to return the damaged joint to its full function.

It is known in the art that non-ablative thermal energy applied to unstable soft tissue, such as collagen tissue, in joints may alter or manipulate the tissue's healing response. In particular, applying controlled thermal energy to damaged soft tissue in a joint can cause the collagenous tissue to shrink, thereby tightening unstable joints.

Medical probes employing heat for the thermal manipulation of soft tissue are known in the art. For example, U.S. Pat. No. 5,458,596 to Lax, et al., discloses examples of a probe with a proximal and distal end that employs heat for the controlled contraction of soft tissue. However, a potential drawback of many prior art probes is that the probe's temperature can become unstable when heat from the probe is dissipated into the mass of the treated tissue. This situation can be a particular problem when treating dense tissue; dense tissue acts as a heat sink thereby requiring additional energy input to maintain the desired temperature. The application of additional energy in an attempt to compensate for the heat sink effect can cause an underdamped effect before settling out at the correct temperature.

In general, a system is underdamped when its damping factor is less than 1. A system is critically damped when its damping factor is exactly 1. And, a system is overdamped when its damping factor is greater than 1. Curve A in FIG. 6 illustrates a typical time-temperature response curve for an underdamped prior art heat application probe. The underdamping shown in curve A results from a system with a very small damping factor—for example, a damping factor less than 0.5.

The "ringing" shown in curve A is a problem because it can cause the momentary application of temperatures that are too high for the safe heating of soft tissue. When this occurs, the soft tissue may be further damaged by being charred or ablated. One reason for the difficulties of prior art probes in providing smooth and consistent heating is that preferred materials for the energy delivery electrodes are highly thermally responsive materials. Such materials generally do not store large amounts of heat energy so that overshoot at initiation (from rapid heating to achieve operating temperature) and underdamped fluctuations during application (often from contact with large tissue masses) present control difficulties.

There is, therefore, a need in the art for an inexpensive and disposable instrument for heating soft tissues that maintains greater control and more constant temperature while initiating and applying treatment.

SUMMARY OF THE INVENTION

Based on the foregoing, an object of the invention is to provide a tissue heating probe that will maintain a more constant temperature while initiating and applying thermal applications to targeted soft tissues.

This and other objects are achieved according to the present invention by a medical instrument that includes an elongated body portion with a proximal and distal end and two cooperative heating sources. The first heating source is preferably disposed on the distal end of the elongated body. In the preferred embodiment, the first heating source is an RF electrode. The second heating source is preferably disposed proximally behind the first heating source and provides secondary heat to the first heating source. The first heating source is chosen to provide a more rapid thermal response than the second heating source. The second heating source is chosen such that it has a higher heat capacity than the first heating source, such that the temperature fluctuations in the first heating source are dampened or compensated for by the second heating source.

DETAILED DESCRIPTION OF THE INVENTION

The structure and function of the preferred embodiments can best be understood by reference to the drawings. The reader will note that the same reference designations appear in multiple locations. Where this is the case, the numerals refer to the same or corresponding structure in those locations.

Figure 1:
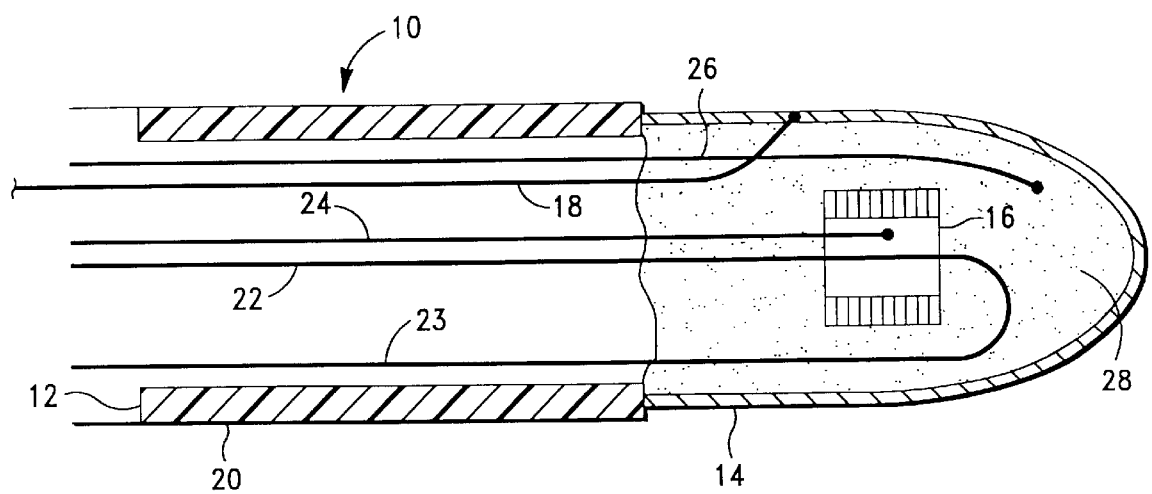
FIG. 1 is a schematic cross-sectional view of a tissue heating probe according to a first embodiment of the present invention.

FIG. 1 shows a tissue heating probe 10, according to a first embodiment of the present invention, which includes an elongated body 12, first heating source 14 (an RF electrode) and a second heating source 16. Elongated body 12 has a proximal and distal end, the distal end being illustrated. RF electrode 14 is a first heating source for tissue heating probe 10. Preferably, elongated body 12 is hollow, conductive, and flexible or malleable. RF electrode 14 is disposed at the distal end of elongated body 12. An optional surface on RF electrode 14 can be created with silver, copper, gold, aluminum, or the like to enhance its conductive properties. Also, RF electrode 14 may have a non-stick coating such as teflon or the like. RF electrode 14 is electrically connected to a first RF power source via a conductor 18. A common ground may be provided by a remote electrode placed on the patient.

An insulative sleeve 20 is disposed on elongated body 12 of tissue heating probe 10. The insulative sleeve 20 exposes at least a portion of RF electrode 14 which is located at the distal end of tissue heating probe 10 and otherwise protects conductive elongated body 12 against contact with tissue. Insulative sleeve 20 can be made out of any insulative material with the appropriate properties. Typical insulative materials include rubber, glass, specially made polymers and the like. Details of probe 10 as described to this point are set forth more fully in U.S. Pat. No. 5,458,596, which is incorporated by reference herein.

Second heating source 16 is located in or near the distal end of tissue heating probe 10. Second heating source 16 provides the probe with a cooperative heating source that works in conjunction with RF electrode 14. Second heating source 16 is generally an inductive heating source and preferably is a higher heat capacity material which is capable of storing larger amounts of heat energy as compared to electrode 14 and thus has a slower response time for temperature fluctuations. Suitable materials include a contained liquid, such as saline, or an electrothermal mass such as a ferrite, resistive element, toroid, or the like.

In the embodiment of FIG. 1, second heating source 16 is an electrothermal mass. This electrothermal mass is excited when conductor 22, 23 receives input from a second power source. This second power source may be an independent power source or a separately controlled output of the first RF power source. When the second power source excites conductor 22, 23 it causes a current to be induced in second heating source 16. This induced current causes second heating source 16 to heat up. A constant supply of power to conductor 22, 23 will result in a constant current in second heating source 16, thus a constant temperature. Similarly, an increase in the power supplied to conductor 22, 23 will result in an increased current in second heating source 16, thus an increased temperature. Conductor 22, 23 may be a wire, a conductive coil, or the like. In a preferred embodiment, the electrothermal mass is a ferrite toroid, although it will be appreciated by persons skilled in the art that other shapes may be used. The properties of ferrite when placed in a field as created by conductor 22, 23 are understood in the art and the dimensions of the ferrite and conductor may be selected in combination with desired power levels to provide appropriate heating.

A first thermocouple 24 is disposed near second heating source 16. First thermocouple 24 may be disposed through an opening in second heating source 16 or otherwise located adjacent to second heating source 16 so as to be indicative of its temperature. First thermocouple 24 creates the feedback required to maintain second heating source 16 at a desired temperature. The power supplied to conductor 22, 23 is adjusted according to the temperature of second heating source 16 as measured by first thermocouple 24.

An optional second thermocouple 26 may be disposed immediately adjacent to RF electrode 14. Second thermocouple 26 may be used to monitor the temperature at the distal end of tissue heating probe 10.

An optional conductive paste 28 may be generally disposed in the distal end of tissue heating probe 10. Conductive paste 28 facilitates even heat conduction between RF electrode 14 and second heating source 16. The cooperation between second heating source 16, RF electrode 14, and, where applicable, conductive paste 28, maintains an even and reliable temperature to tissue heating probe 10.

When the conductive surface of RF electrode 14 comes in contact with the soft tissue being treated, the tissue may have a tendency to sink heat away as previously described. Second heating source 16 maintains a secondary and more constant heat supply at the distal end of tissue heating probe 10 such that when soft tissue sinks heat away from the distal end of RF electrode 14, RF electrode 14 begins to sink heat away from second heating source 16. This cooperative heating maintains a more constant and predictable heat to the distal end of RF electrode 16. The use of the heating sources also allows much greater control at start up by permitting the probe to be brought up to operating temperature while reducing overshoot typically associated with the rapid response of RF electrode 14 alone.

Figure 1A:
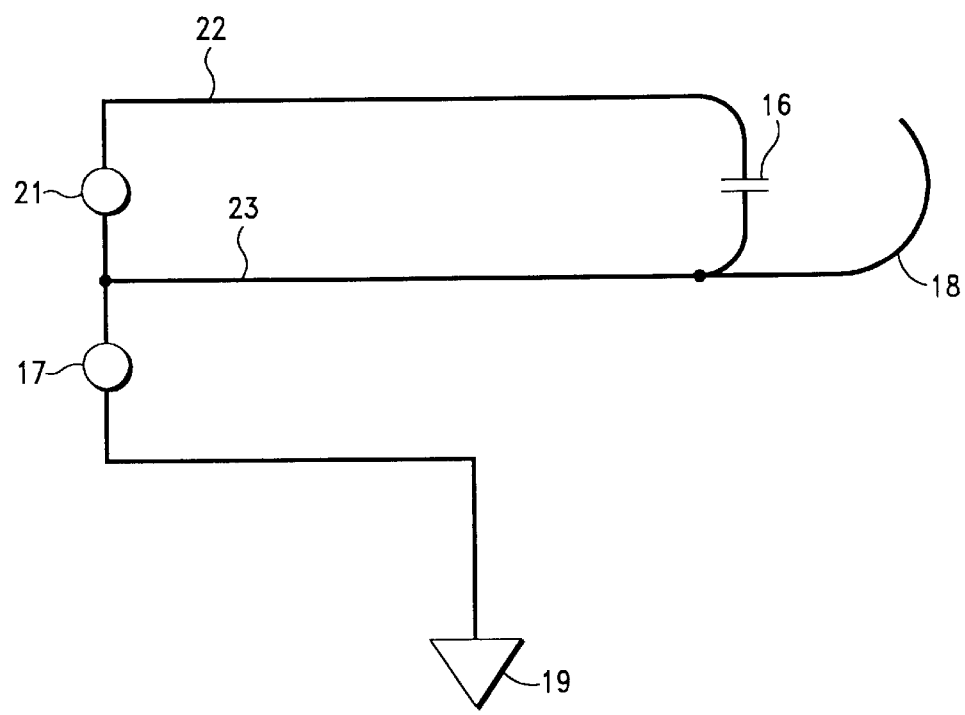
FIG. 1A is an electrical schematic of the electrical circuits for the tissue heating probe of FIG. 1.

FIG. 1A is an electrical schematic of the electrical circuits for the tissue heating probe of FIG. 1. Power supply 21 supplies power to conductors 22, 23 which pass by second heating source 16, shown here as a capacitor, although a resistor or inductor may also be possible as will be described in other embodiments of the present invention. Power source 17 supplies power to conductor 18 which powers RF electrode 14. This circuit is completed by a remote grounding electrode 19 which is attached to the patient. It should be appreciated that while this schematic represents an example of how the power supplies and circuits may be connected, a person of skill in the art will appreciate that other electrical designs are possible. In particular, it should be appreciated that separate or common power sources may be used for the RF electrode and the second heating source.

Figure 2:
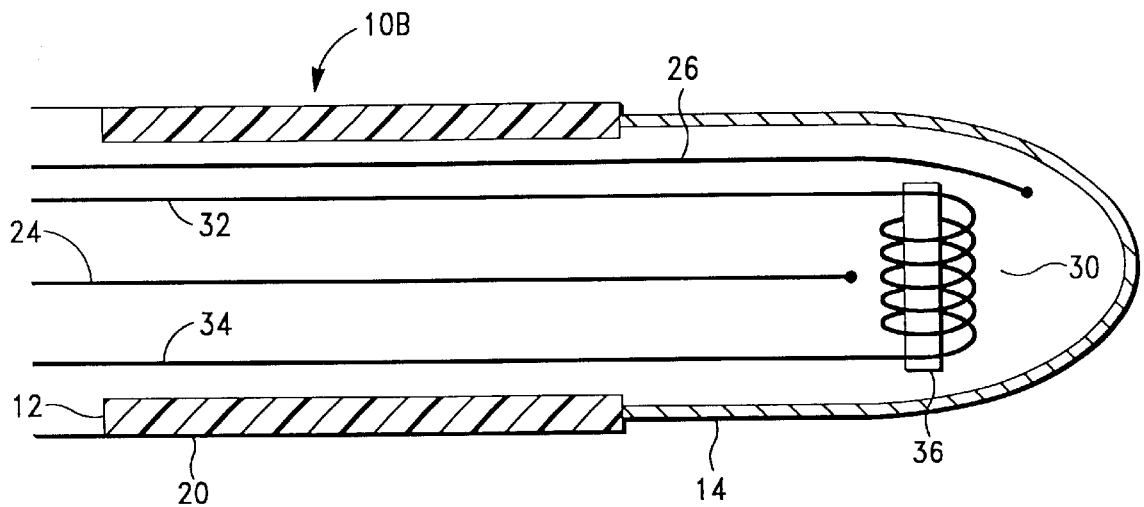
FIG. 2 is a schematic cross-sectional view of a tissue heating probe according to an alternative embodiment of the present invention.

FIG. 2 shows a tissue heating probe 10A according to an alternative embodiment. The embodiment of FIG. 2 encompasses elongated body 12, RF electrode 14, thermocouples 24 and 26, and insulative sleeve 20, as described in FIG. 1 above. Here, the second heating source is a heating coil 30 connected to conductors 32 and 34. Heating coil 30 can be a single wound coil, a combination of multiple coils, a toroid, a combination of toroids, or the like. Heating coil 30 is electrically connected via conductors 32 and 34 to a second power source as that described above in connection with FIG. 1. Heat storing material 36 is generally disposed through heating coil 30. Heat storing material 36 may be an electrothermal mass or a contained liquid. In a preferred embodiment material 36 is a ferrite rod. Power applied to heating coil 30 induces a current into heat storing material 36 thereby causing a rise in the temperature of heat storing material 36. It should be appreciated that conductive paste 28 may optionally be disposed in the distal end of tissue heating probe 10A.

Figure 3:
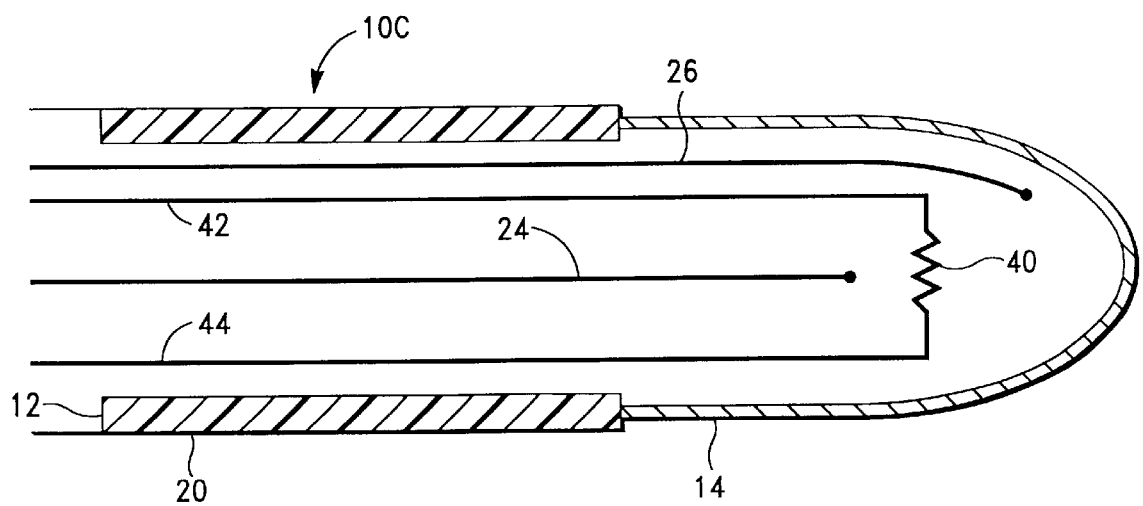
FIG. 3 is a schematic cross-sectional view of a tissue heating probe according to an additional alternative embodiment of the present invention.

FIG. 3 shows a tissue heating probe 10C according to another alternative embodiment. The embodiment of FIG. 3 encompasses elongated body 12, RF electrode 14, thermocouples 24 and 26, and insulative sleeve 20, as described in FIG. 1 above. In this embodiment, the second heating source comprises resistive element 40 connected to a suitable power source via conductors 42 and 44. Again, conductive paste 28 (not shown) may also be used.

Figure 4:
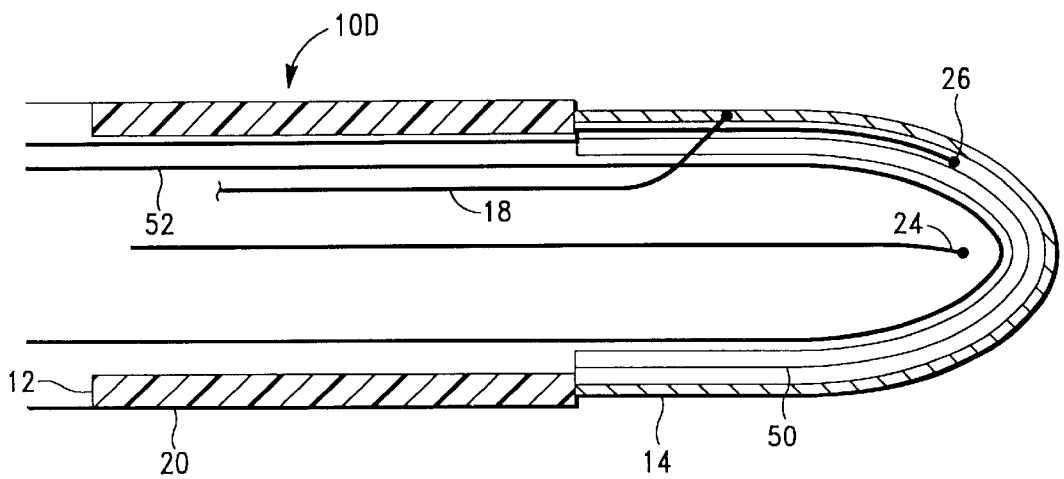
FIG. 4 is a schematic cross-sectional view of a tissue heating probe according to yet another additional alternative embodiment of the present invention.

FIG. 4 shows a tissue heating probe 10D according to another alternative embodiment. The embodiment of FIG. 4 again includes elongated body 12, RF electrode 14, thermocouples 24 and 26, conductor 18, and insulative sleeve 20. In this embodiment, second heating source is contained liquid 50. The liquid may be contained in a tubular structure that is sealed at both ends; however, it should be appreciated that any manner of containing the liquid in the tip of the probe may be used. Furthermore, containing the liquid in any portion of the tip of the probe may be used. The tubular structure may be malleable so that it may be fitted inside the distal end of tissue heating probe 10D and proximally behind RF electrode 14. The liquid in the contained liquid 50 can be any suitable electrolyte or conductive fluid or gel, such as saline, sodium bromide, sodium sulfate, sodium nitrate, potassium bromide, potassium sulfate, potassium nitrate, caesium bromide, caesium sulfate, caesium nitrate, magnesium bromide, magnesium sulfate, magnesium nitrate, calcium bromide, calcium sulfate, calcium nitrate, or the like.

Conductor 52 receives power from a second power source. Contained liquid 50 is heated as a result of the induced current from conductor 52. Once heated, the contained liquid 50 cooperates with RF electrode to maintain tissue heating probe 10D within a desired temperature band, as previously described.

In a further alternative embodiment, rather than electrically heating liquid 50, the liquid may be continuously provided in a heated condition. In this embodiment, appropriately sized tubes for continuous delivery of heated liquid would replace conductor 52.

Figure 4A:
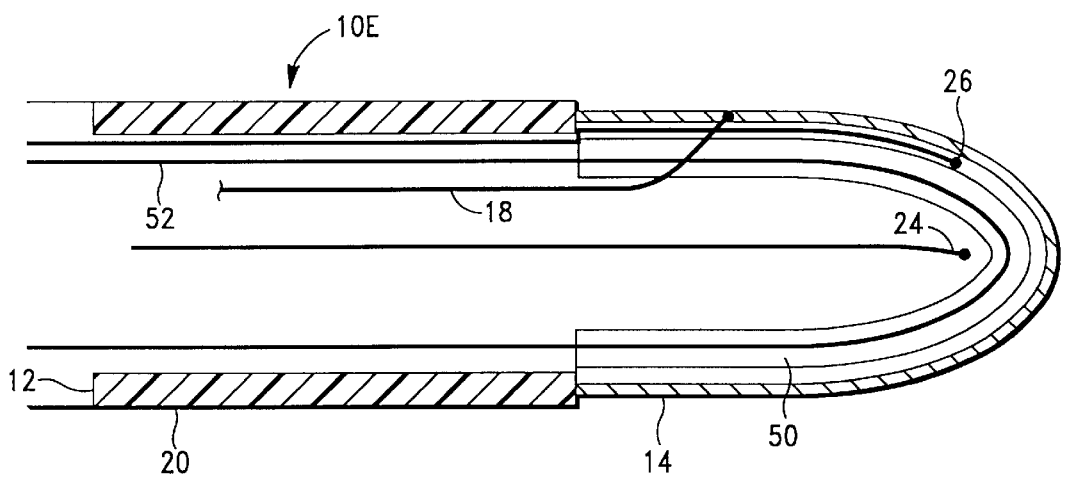
FIG. 4A is a schematic cross-sectional view of a tissue heating probe according to yet another additional alternative embodiment of the present invention.

FIG. 4A is a schematic cross-sectional view of a tissue heating probe according to yet another additional alternative embodiment of the present invention. FIG. 4A shows probe 10E which is similar to probe 10D shown in FIG. 4 in that second heating source is contained liquid 50 which may be contained in a tubular structure that is sealed at both ends. In this embodiment, however, conductor 18 passes through the liquid 50 such that liquid 50 acts as a dieletric.

Figure 5:
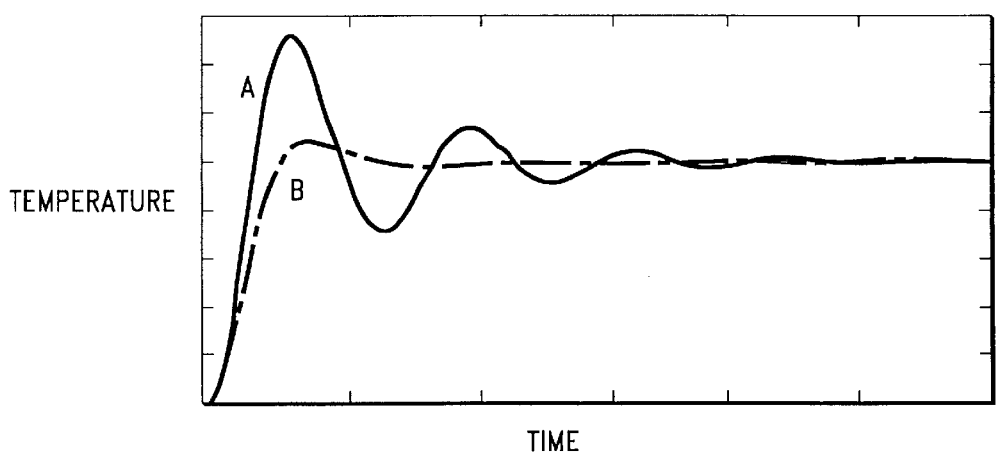
FIG. 5 is a graphical display of system responses.

Referring to FIG. 5, curve B generally describes the start up and operating conditions of the tissue heating probe according to the invention. Curve B displays a slightly underdamped system operating condition wherein the system preferred damping factor is slightly less than one. A slightly underdamped system may provide the advantages of stability inherent in a critically damped system with a faster overall heating response. However, one skilled in the art may select a critically damped system which would also be adequate. The rise and fall time as well as the variation in the operating temperature will vary according to the heat transfer equation defining the system's overall design. In a preferred embodiment, the heat transfer equation will be a multi-function equation likely including at least two poles. In the typical case, the dominant pole will likely be defined by the temperature response of RPF electrode 14, which will vary according to such factors as size and material. Similarly, the second pole will likely be defined by the temperature response of second heating source 16. The heat transfer equation will also dictate such criteria as temperature stability at the distal end of RF electrode 14 during use. For example, the poles of the heat transfer function can be selected such that the variation in temperature at the distal end of the tissue heating probe is limited to a temperature band as narrow as three to five degrees. The overall system temperature response is limited by design factors including size, material, available power supply and cost.

It should be understood that the descriptions provided herein are meant to provide examples of preferred embodiments of the present invention and are not meant to limit the scope of the invention. One skilled in the art may provide variations or modifications without deviating from the present invention. For example, various materials, power sources or controls may be used by a person of ordinary skill in the art without departing from the scope of the invention as stated in the appended claims.

What is claimed is:

1. A tissue heating apparatus, comprising:
   an elongated body having proximal and distal ends;
   a first heating source disposed on the distal end of said elongated body to deliver heat to a tissue to be treated; and
   a second heating source disposed adjacent said first heating source to provide secondary heat to the tissue simultaneously as said first heating source delivers heat to the tissue;
   wherein said first heating source provides a more rapid thermal response than said second heating source and said second heating source has a higher heat capacity than said first heating source such that temperature fluctuations in said first heating source are dampened by said second heating source, and wherein said second heating source comprises an electrothermal mass.

2. The tissue heating apparatus of claim 1, wherein said electrothermal mass comprises a cylindrically shaped ferrite bead having at least one longitudinal opening spanning the length of said ferrite bead.

3. The tissue heating apparatus of claim 1, wherein said electrothermal mass comprises a toroid having annular shape.

4. The tissue heating apparatus of claim 1, wherein said electrothermal mass comprises a resistive element.

5. The tissue heating apparatus of claim 1, wherein said electrothernal mass comprises a liquid disposed within a sealed container.

6. The tissue heating apparatus of claim 1, wherein said electrothermal mass source comprises a coil.

7. The apparatus of claim 6, further comprising an additional electrothermal mass positioned within said coil.

8. The apparatus of claim 1, wherein said second heating source comprises a heated liquid circulated through said distal end.

9. The apparatus of claim 1, wherein said first heating source comprises an RF electrode disposed on the distal end of said body.

10. The apparatus of claim 1, further comprising a first thermocouple disposed within said elongated body to sense the temperature of the second heating source.

11. The tissue heating apparatus of claim 10, further comprising:
    a second thermocouple, said second thermocouple located proximally behind said first heating source, such that said second thermocouple primarily responds according to the temperature of said first heating source.

12. A tissue heating apparatus, comprising:
    an elongated body having proximal and distal ends;
    a first heating source disposed on the distal end of said elongated body to deliver heat to a tissue to be treated;
    a second heating source disposed adjacent said first heating source to provide secondary heat to said first heating source; and
    a conductor having a portion adjacent to said second heating source such that said conductor induces a current into said second heating source when power is applied to the conductor;

wherein said first heating source provides a more rapid thermal response that said second heating source and said second heating source has a higher heat capacity than said first heating source such that temperature fluctuations in said first heating source are dampened by said second heating source.

13. A tissue heating apparatus, comprising:

an elongated body having proximal and distal ends;

a first heating source disposed on the distal end of said elongated body to deliver heat to a tissue to be treated;

a second heating source disposed adjacent said first heating source to provide secondary heat to said first heating source; and a conductive paste, disposed within the distal end of said tissue heating apparatus to facilitate an even distribution of heat between said second heating source and said first heating source;

wherein said first heating source provides a more rapid thermal response than said second heating source and said second heating source has a higher heat capacity than said first heating source such that temperature fluctuations in said first heating source are dampened by said second heating source.

14. A tissue heating apparatus, comprising:

an elongated body having proximal and distal ends;

a first heating source disposed within the distal end of said elongated body to deliver heat to a tissue to be treated; and a second heating source disposed within said elongated body proximally behind said first heating source to provide secondary heat to said first heating source wherein said first heating source provides a more rapid thermal response than said second heating source and said second heating source has a higher heat capacity than said first heating source such that temperature fluctuations in said first heating source are dampened by said second heating source, wherein said elongated body defines a hollow distal end with a heat conductive paste being disposed with said distal end in contact with said first and second heating sources.

15. The tissue heating apparatus of claim 14, wherein said first heating source comprises an RF electrode.

16. A tissue heating apparatus, comprising:

an elongated body having proximal and distal ends;

a first heating source disposed on the distal end of said elongated body to deliver heat to a tissue to be treated; and a second heating source disposed within said elongated body proximally behind said first heating source to provide secondary heat to said first heating source wherein said first heating source provides a more rapid thermal response than said second heating source and said second heating source has a higher heat capacity than said first heating source such that temperature fluctuations in said first heating source are dampened by said second heating source, wherein said second heating source comprises an electrothermal mass with a conductor passing in close proximity thereto so as to induce a current in said mass in response to power applied to said conductor.

17. The apparatus according to claim 16, wherein said electrothermal mass comprises a ferrite cylinder with said conductor passing through an opening therein.

18. A soft tissue heating apparatus, comprising:

an elongated body with proximal and distal ends;

an RF electrode disposed on the distal end of said elongated body to deliver heat to a tissue to be treated;

a separate heating source disposed within said distal end proximally behind said RF electrode to provide secondary heat to said RF electrode, said heating source comprising a ferrite mass; and a conductor positioned in close proximity to said ferrite mass to induce a heating current therein in response to applied power.

* * * * *